United States Patent
Hess (10) Patent No.: US 8,442,627 B2
(45) Date of Patent: May 14, 2013

(54) ADVANCED THORACIC FLUID MONITORING CAPABILITY WITH IMPEDANCE

(75) Inventor: Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 2680 days.

(21) Appl. No.: 11/322,700

(22) Filed: Dec. 30, 2005

(65) Prior Publication Data

US 2007/0156061 A1 Jul. 5, 2007

(51) Int. Cl.
- *A61B 5/05* (2006.01)
- *A61B 5/02* (2006.01)
- *A61B 5/08* (2006.01)
- *A61B 5/103* (2006.01)
- *A61B 5/117* (2006.01)

(52) U.S. Cl.
USPC ........... 600/547; 600/483; 600/533; 600/536; 600/587; 600/595

(58) Field of Classification Search .................. 600/547, 600/587, 595, 533, 536, 483; 607/9, 11, 607/19; 623/3.1, 3.28
See application file for complete search history.

(56) References Cited

U.S. PATENT DOCUMENTS

| | | | |
|---|---|---|---|
| 4,374,382 A | 2/1983 | Markowitz | |
| 5,107,833 A | 4/1992 | Barsness | |
| 5,168,871 A | 12/1992 | Grevious | |
| 5,292,343 A | 3/1994 | Blanchette et al. | |
| 5,314,450 A | 5/1994 | Thompson | |
| 5,324,315 A | 6/1994 | Grevious | |
| 5,354,319 A | 10/1994 | Wyborny et al. | |
| 5,383,909 A | 1/1995 | Keimel | |
| 5,876,353 A * | 3/1999 | Riff | 600/547 |
| 6,104,949 A * | 8/2000 | Pitts Crick et al. | 600/547 |
| 6,128,534 A | 10/2000 | Park et al. | |
| 6,658,292 B2 * | 12/2003 | Kroll et al. | 607/19 |
| 6,731,984 B2 | 5/2004 | Cho et al. | |
| 6,752,765 B1 * | 6/2004 | Jensen et al. | 600/536 |
| 6,922,592 B2 | 7/2005 | Thompson et al. | |
| 7,226,422 B2 * | 6/2007 | Hatlestsad et al. | 600/534 |
| 2004/0138716 A1 | 7/2004 | Kon et al. | |
| 2004/0172080 A1 | 9/2004 | Stadler et al. | |
| 2006/0258952 A1 * | 11/2006 | Stahmann et al. | 600/547 |

FOREIGN PATENT DOCUMENTS

| | | |
|---|---|---|
| EP | 0985429 A | 3/2000 |
| EP | 1731088 A | 12/2006 |
| WO | WO9833554 A | 8/1998 |
| WO | WO20040045406 A | 6/2004 |
| WO | WO20050046472 A | 5/2005 |

OTHER PUBLICATIONS

International Search Report, PCT/US2006/062210, Jul. 1, 2008, 6 pages.

* cited by examiner

*Primary Examiner* — Sean P Dougherty
*Assistant Examiner* — Devin Henson
(74) *Attorney, Agent, or Firm* — Reed Duthler; Stephen W. Bauer (57) ABSTRACT

An implantable medical device used for thoracic fluid monitoring by detection of changes in impedance in a patient. The device measures impedances of the patient in a supine position and in an upright position. The device determines impedance differences between the supine and upright positions which correspond to a diurnal delta value, which may in turn be employed as a diagnostic parameter.

7 Claims, 8 Drawing Sheets

ADVANCED THORACIC FLUID MONITORING CAPABILITY WITH IMPEDANCE

BACKGROUND

The present invention relates to medical devices, and, more particularly, to implantable medical device.

Impedance monitoring has been used with implanted devices and in external monitoring devices for determination of numerous physiologic conditions. Transthoracic impedance measurements give a good indication of the fluid status of patients, with decreases in impedance being indicative of increases in fluid content. Knowledge of a patient's long-term impedance measurements and changes therein are a valuable clinical indicator of a patient's health.

While a possible indication of other conditions, the accumulation of fluid can also indicate failing heart circulation. There are several mechanisms or diseases that can cause or affect the accumulation of fluid. In general, fluid accumulation is a failure or over-response of the homeostatic process within the body. The body normally prevents the build up of fluids by maintaining adequate pressures and concentrations of salt and proteins and by actively removing excess fluid. Fluid accumulation can occur, for example, when the body's mechanisms for preventing fluid accumulation are affected by disease, such as heart failure, left sided myocardial infarction, high blood pressure, altitude sickness, emphysema (all which affect pressures), cancers that affect the lymphatic system, and diseases that disrupt the protein concentrations. As a result, providing an adequate monitor of the patient's fluid status can provide physicians and patients with a better tool to manage disease.

However, impedance monitoring sensitivity to intestine and other peripheral edema is not currently known. It is speculated that impedance monitoring during the time when a patient is upright, for example noon till 5 p.m., normalizes postural changes that would otherwise confound the impedance measurement. Further, upright monitoring may also mask earlier warning signs that may be evident if the impedance monitoring was performed in other patient body positions.

Presently there are devices which track impedance changes in a patient over time and monitor for deviations that would be consistent with fluid overload. To maintain good specificity the algorithm only uses data collected between 12 pm and 5 pm each day. This standardization is intended to eliminate postural variability that could confound the trending algorithm.

Patients who are retaining too much fluid have a greater problem with pulmonary congestion when supine as opposed to when standing or sitting. Many patients for example must sleep with multiple pillows elevating their head to displace fluid to their lower extremities. As more fluid is retained this problem becomes greater, as the extremities are less capable of absorbing the volume.

DESCRIPTION OF VARIOUS EMBODIMENTS

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention.

Figure 1:
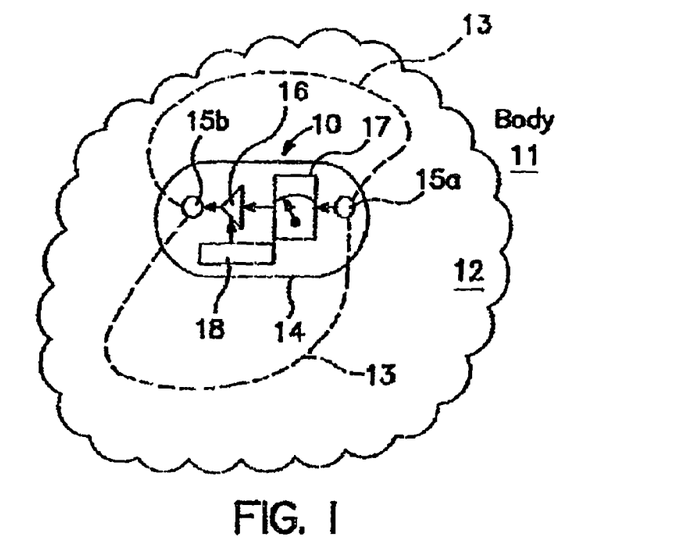
FIG. 1 is a schematic diagram of an implantable medical device according to an embodiment of the present invention.

FIG. 1 is a schematic diagram of an implantable medical device according to an embodiment of the present invention. In the heuristic drawing of FIG. 1, a section of a body 11 is shown with a cut-away area 12 to allow for illustration of an implantable medical device according to an embodiment of the present invention. As illustrated in FIG. 1, an exemplary embodiment of an implantable medical device 10 includes two electrodes 15a and 15b on the surface of a shell 14 of device 10. Power is provided to the circuitry internal to the shell 14 by a power supply 18, which drives a stimulation circuit 16, sending electrons through various pathways in the body between electrodes 15a and 15b. The pathways are heuristically illustrated as being primarily in the area surrounded by dotted line 13. An impedance measurement device 17 determines the impedance of the circuit pathway 13.

Figure 2:
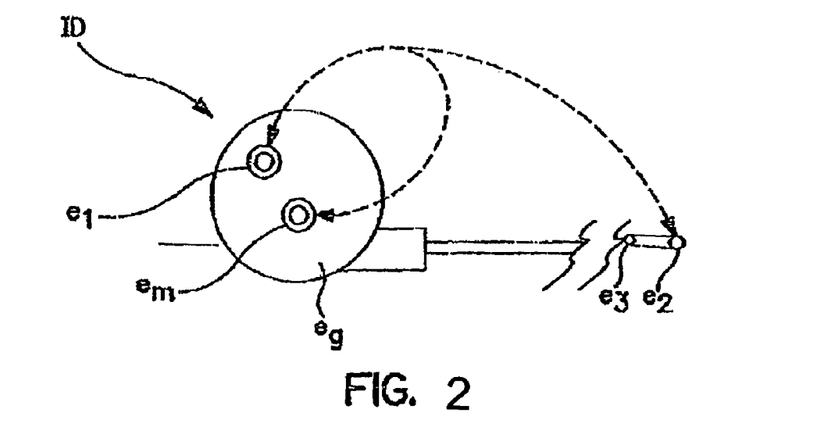
FIG. 2 is a schematic diagram of exemplary electrode configurations in an implantable medical device according to an embodiment of the present invention.

FIG. 2 is a schematic diagram of exemplary electrode configurations in an implantable medical device according to an embodiment of the present invention. This acceptable variety of configuration to achieve different impedance measurement signal values is illustrated, for example, in FIG. 2 wherein an implantable medical device includes electrodes (e1), (e2), (eg) and (em) and either electrodes (e1) or (e2) can be used for developing the test pulses. The value being measured (voltage or impedance of the tissue between these electrode pairs) is taken between another electrically isolated measuring electrode (em) and the indifferent or ground electrode (eg), between (em) and (e1), or between (em) and (e2). Or, of course, the measurement could be taken between the two test pulse delivery electrodes (e1), and (eg), or between (e2) and (eg) in another embodiment.

Figure 3:
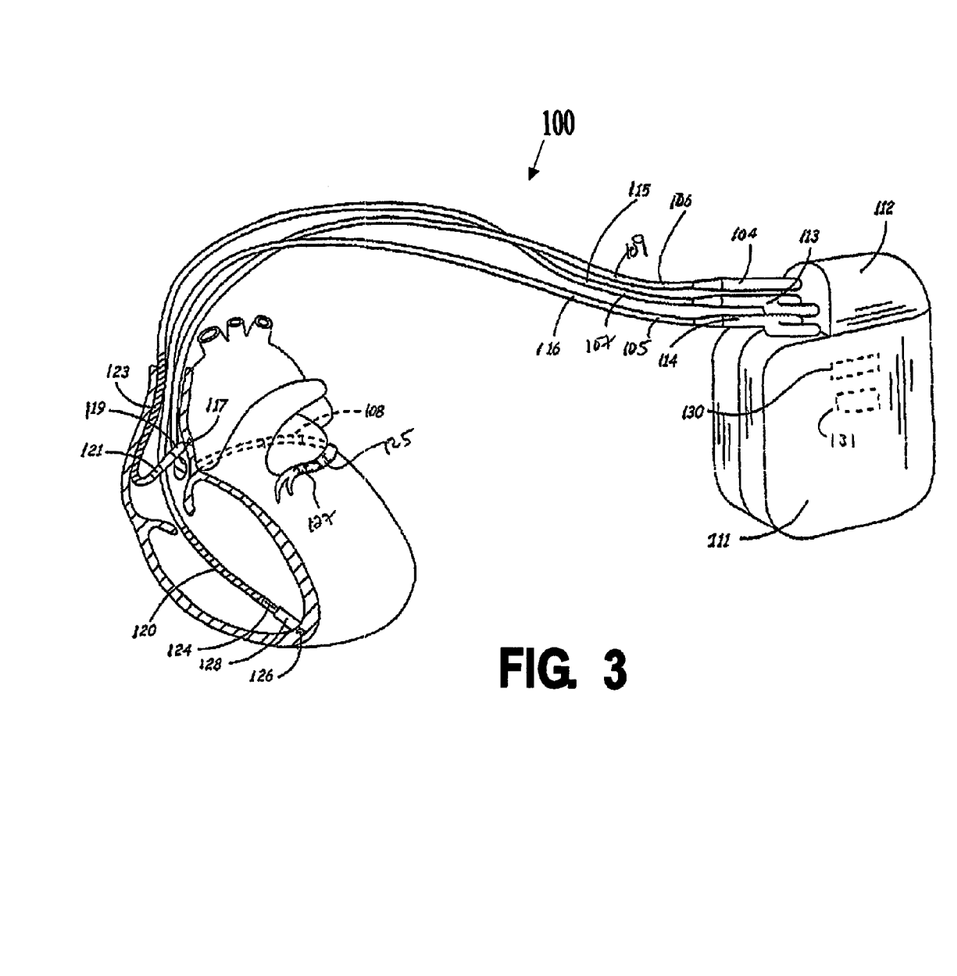
FIG. 3 is a schematic diagram of an implantable medical device in which the present invention may usefully be practiced according to an embodiment of the present invention.

FIG. 3 is a schematic diagram of an implantable medical device in which the present invention may be practiced according to an embodiment of the present invention. As illustrated in FIG. 3, an implantable medical device 100 according to an embodiment of the present invention includes a ventricular lead 105 having an elongated insulative lead body 116 carrying three mutually insulated conductors. Located adjacent the distal end of the lead 105 are a ring electrode 124, an extendable helix electrode 126 mounted retractably within an insulative electrode head 128, and an elongated coil electrode 120. Each of the electrodes 120, 124 and 126 is coupled to one of the three conductors within the lead body 116. Electrodes 124 and 126 are employed for cardiac pacing and for sensing ventricular depolarizations, and electrode 120 is employed for cardioversion and/or defibrillation and for sensing depolarizations, as described below. At the proximal end of the lead 105 is a bifurcated connector 114, which carries three electrical connectors, each coupled to one of the coiled conductors.

An atrial/SVC lead 107 includes an elongated insulative lead body 115, also carrying three mutually insulated conductors. Located adjacent the J-shaped distal end of the lead 107 are a ring electrode 121 and an extendible helix electrode 117, mounted retractably within an insulative electrode head 119. Each of the electrodes 117 and 121 is coupled to one of the conductors within the lead body 115. Electrodes 117 and 121 are employed for atrial pacing and for sensing atrial depolarizations. An elongated coil electrode 123 is provided, proximal to electrode 121 and coupled to the third conductor within the lead body 115. At the proximal end of the lead 107 is a bifurcated connector 113, which carries three electrical connectors, each coupled to one of the coiled conductors.

A coronary sinus/coronary vein lead 109 includes an elongated insulative lead body 106, carrying three conductors, one of which is coupled to an elongated coiled defibrillation electrode 108. Electrode 108, illustrated in broken outline, is located within the coronary sinus and great vein of the heart. Located adjacent the distal end of lead 109 are a ring electrode 125 and a tip electrode 127. Each of electrodes 125-127 is coupled to one of the remaining two of the three conductors located within lead body 106. At the proximal end of the lead 109 is a connector plug 104 that carries an electrical connector, coupled to the coiled conductors.

The implantable medical device 100 includes a hermetically sealed enclosure 111 containing the electronic circuitry (FIG. 4) used for generating cardiac pacing pulses for delivering cardioversion and defibrillation shocks and for monitoring the patient's heart rhythm. Implantable medical device 110 is shown with the lead connector assemblies 104, 113 and 114 inserted into the connector block 112, which serves as a receptacle and electrical connector for receiving the connectors 104, 113 and 114 and interconnecting the leads to the circuitry within enclosure 111.

Figure 4:
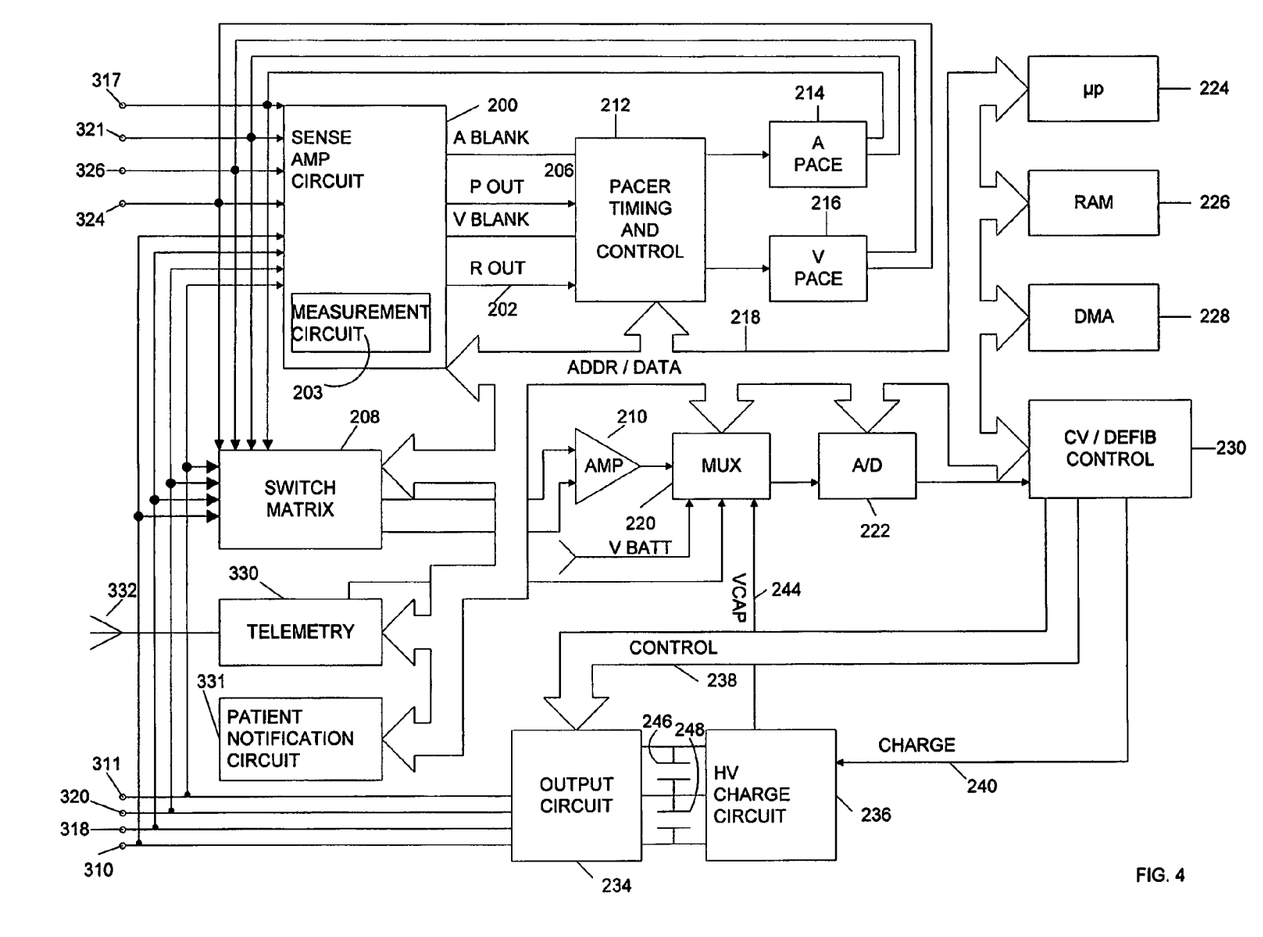
FIG. 4 is a functional block diagram of an exemplary implantable medical device of the type illustrated in FIG. 3, in which the present invention may usefully be practiced.

FIG. 4 is a functional block diagram of an exemplary implantable medical device of the type illustrated in FIG. 3, in which the present invention may usefully be practiced. The device is provided with a lead system including electrodes, such as those illustrated in FIG. 3. Alternate lead systems may of course be substituted. If the electrode configuration of FIG. 3 is employed, the correspondence to the illustrated electrodes is as follows. Electrode 311 corresponds to an electrode formed along the uninsulated portion 130 of the housing of the implantable medical device 110. Electrode 320 corresponds to electrode 120 and is a defibrillation electrode located in the right ventricle. Electrode 310 corresponds to electrode 108 and is a defibrillation electrode located in the coronary sinus. Electrode 318 corresponds to electrode 123 and is a defibrillation electrode located in the superior vena cava. Electrodes 324 and 326 correspond to electrodes 124 and 126, and are used for sensing and pacing in the ventricle. Electrodes 317 and 321 correspond to electrodes 117 and 121 and are used for pacing and sensing in the atrium.

Electrodes 310, 311, 318 and 320 are coupled to high voltage output circuit 234. Electrodes 324 and 326 are coupled to an R-wave amplifier, which preferably takes the form of an automatic gain controlled amplifier providing an adjustable sensing threshold as a function of the measured R-wave amplitude, included in a sense amplifier circuit 200. A signal is generated on R-out line 202 whenever the signal sensed between electrodes 324 and 326 exceeds the present sensing threshold.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits of sense amplifier circuit 200 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their relevant parts, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable antiarrhythmia devices.

Figure 4A:
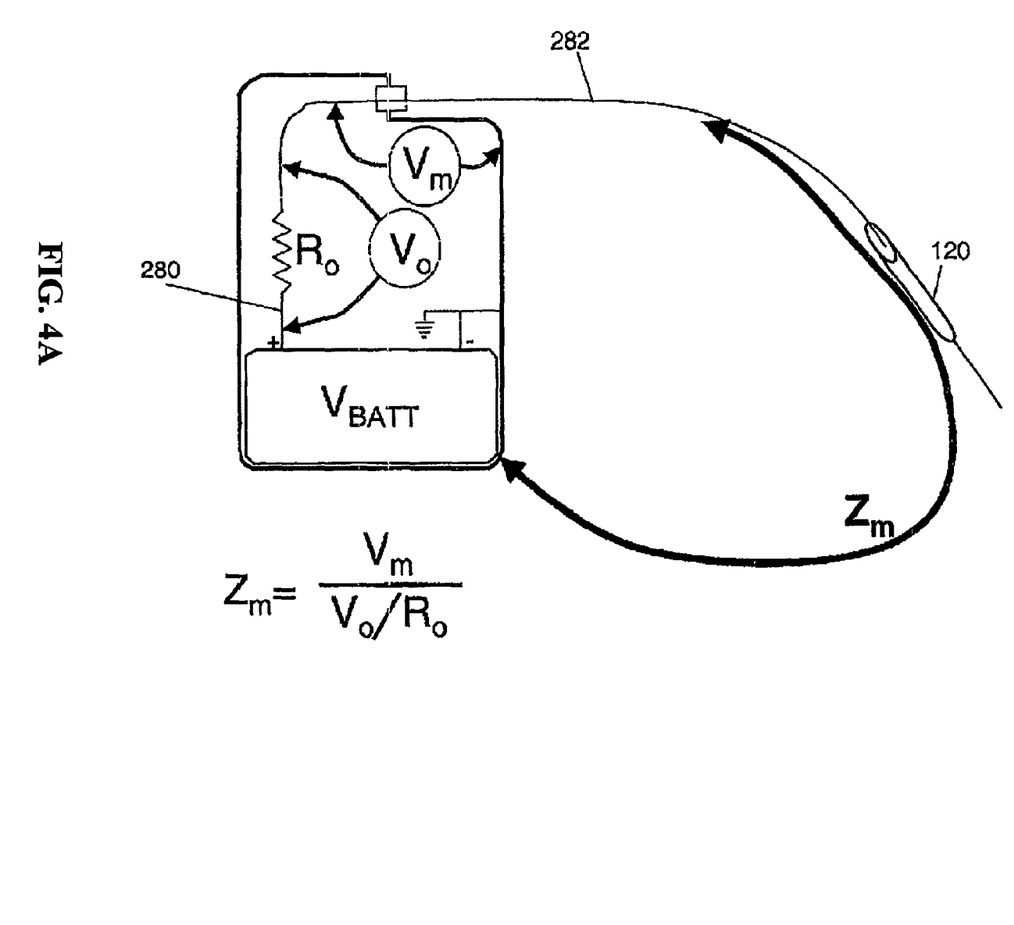
FIG. 4A is a schematic diagram of a method of measuring impedance according to an embodiment of the present invention.

FIG. 4A is a schematic diagram of a method of measuring impedance according to an embodiment of the present invention. For example, according to an embodiment of the present invention, in order to generate a transthoracic impedance $Z_M$ measurement, pacer timing and control circuit 212 initiates, via control circuitry 230, delivery of a predetermined voltage pulse $V_o$ from output circuit 234 along excitation path 280 between electrodes 120 and 130. A resistor $R_o$ incorporated in output circuit 234 is positioned along excitation path 280 having a known resistance so that the current $I_O$ delivered along the excitation path 280 can be calculated, using Ohm's Law, as $I_O=V_o/R_o$. The voltage $V_M$ is measured across the measurement path 282 between a point after resistor $R_o$ and electrode 130, and, knowing the current $I_O$ delivered to the measurement path 282, impedance $Z_M$ is calculated as $Z_M=V_M/(V_o/R_o)$.

According to certain embodiments of the present invention, the average of all impedance measurements acquired over a predetermined time period is calculated to obtain a period average impedance. Values of an expected impedance and a short term average (STA) impedance are computed from the period average impedance, and changes in the period average impedance values over time are monitored for indications of fluid accumulation, as will be described below. The expected impedance is an underlying baseline (BL) impedance that is a very low pass filtered version of the period average impedance and is intended to represent the patient's "dry" impedance when excessive fluid is not present. The value of an expected or baseline impedance varies from patient to patient and is generally between approximately 50 ohms and 90 ohms. The STA impedance is a slightly filtered version of the period average impedance, and is intended to be a best estimate of the current impedance. Once an initial stabilization time period has expired after implantation, the algorithm establishes initial values of the expected, or baseline (BL) impedance, and the short term average (STA) impedance, and begins to search for changes in the impedance measurements.

These measurements may, for example, be obtained from pre-programmed vectors chosen for the excitation path and the measurement path, such as the ring (e3) to case (e2) and tip (e2) to case (eg) arrangement of FIG. 4. The RV coil electrode 120 and housing electrode 130 may, for example, be utilized for both the excitation path and the measurement path described above with reference to FIG. 3. However, it is understood that other arrangements can also be utilized, such as an arrangement in which the excitation path is between electrode 123 and electrode 130 and the measurement path is between electrode 117 and electrode 130. Another operative vector could be an RV coil 120 to can 111 vector with a left pectoral implant. Another could be a vector from an SVC coil 123 and RV coil 120. However, most any vector for impedance monitoring could be used without departing from the spirit of the invention. It is further contemplated the leads can be epicardial leads and/or subcutaneous leads. Can 111 can be implanted in a sub-muscular or subcutaneous location anywhere about the chest however, the location does not have to be in a pectoral region.

Figure 5:
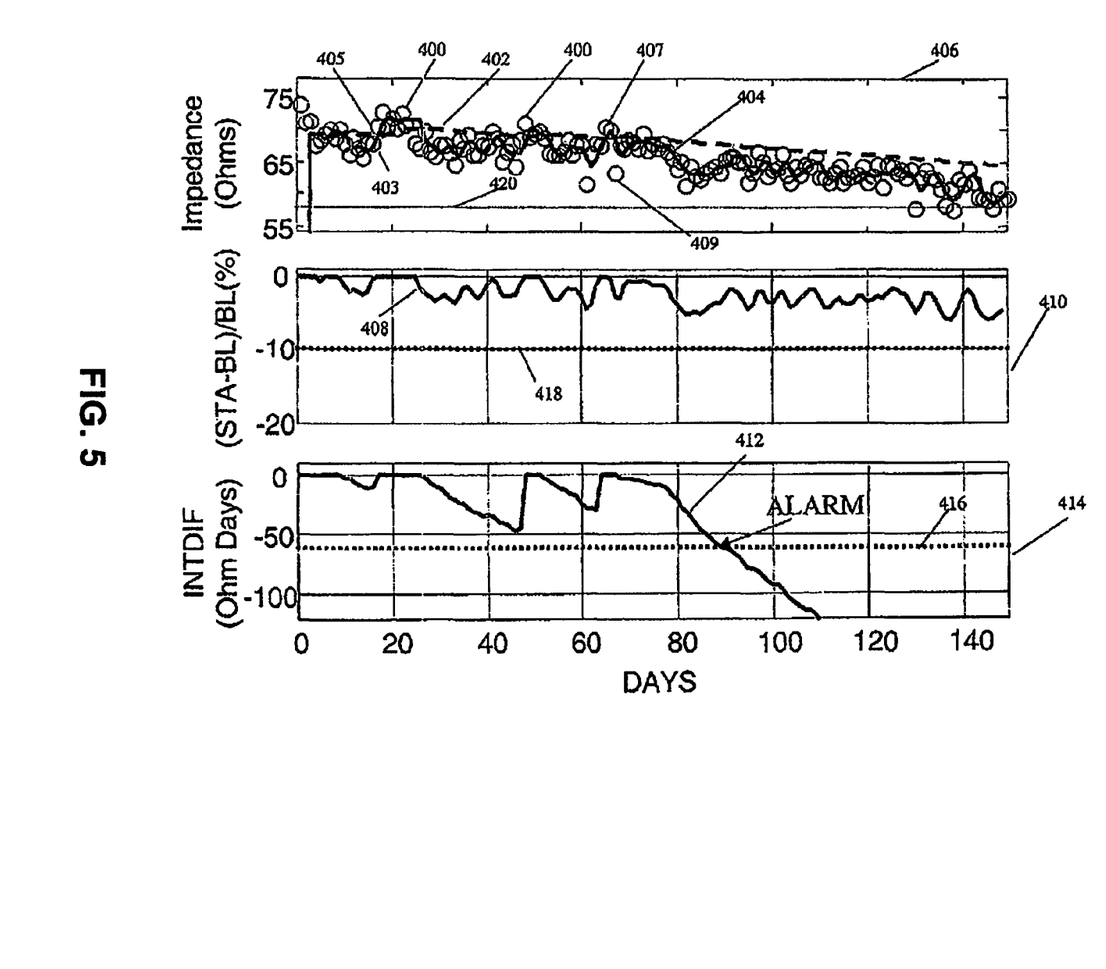
FIG. 5 is an exemplary graphical representation of impedance data generated according to an embodiment of the present invention.
Figure 6:
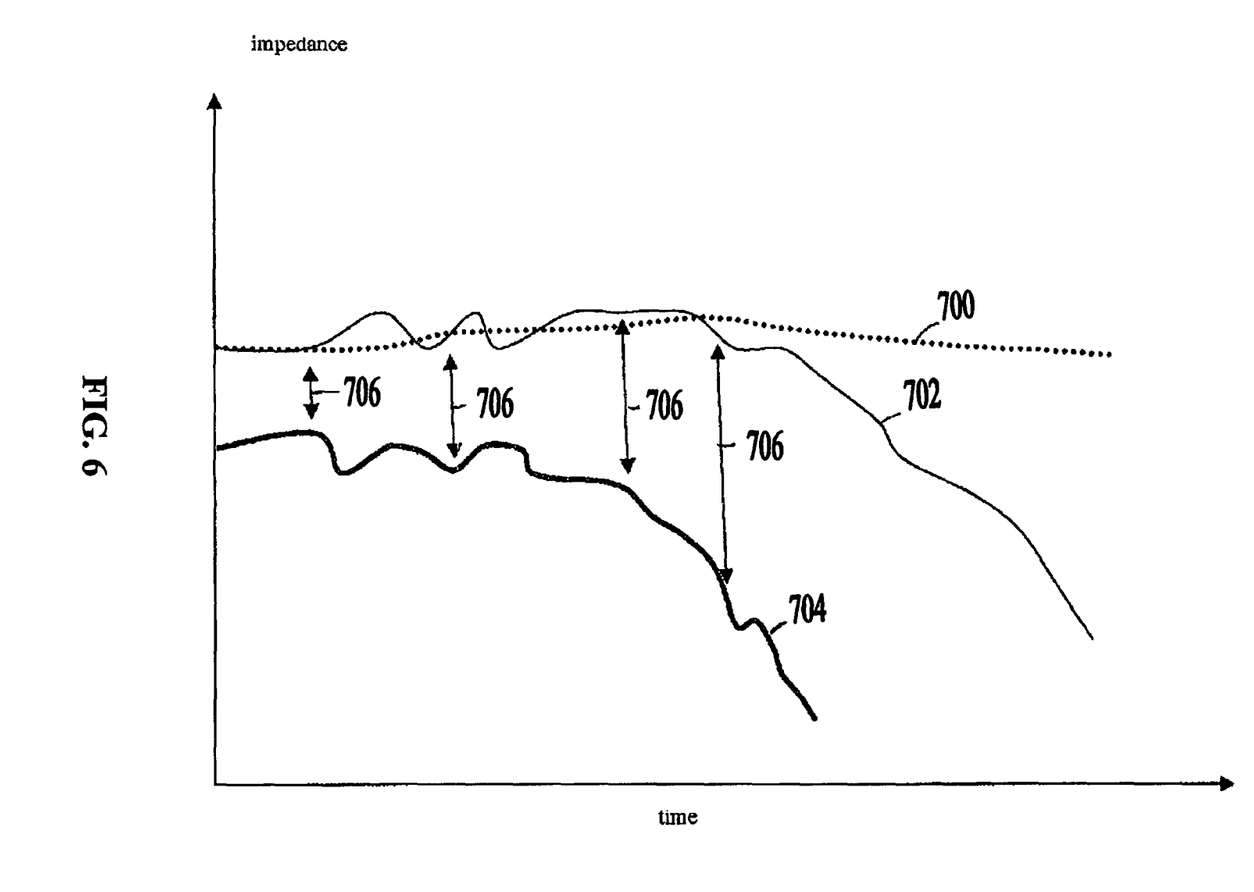
FIG. 6 is a graph showing the behavior between nighttime and daytime impedance measurements in an embodiment of the present invention.
Figure 6A:
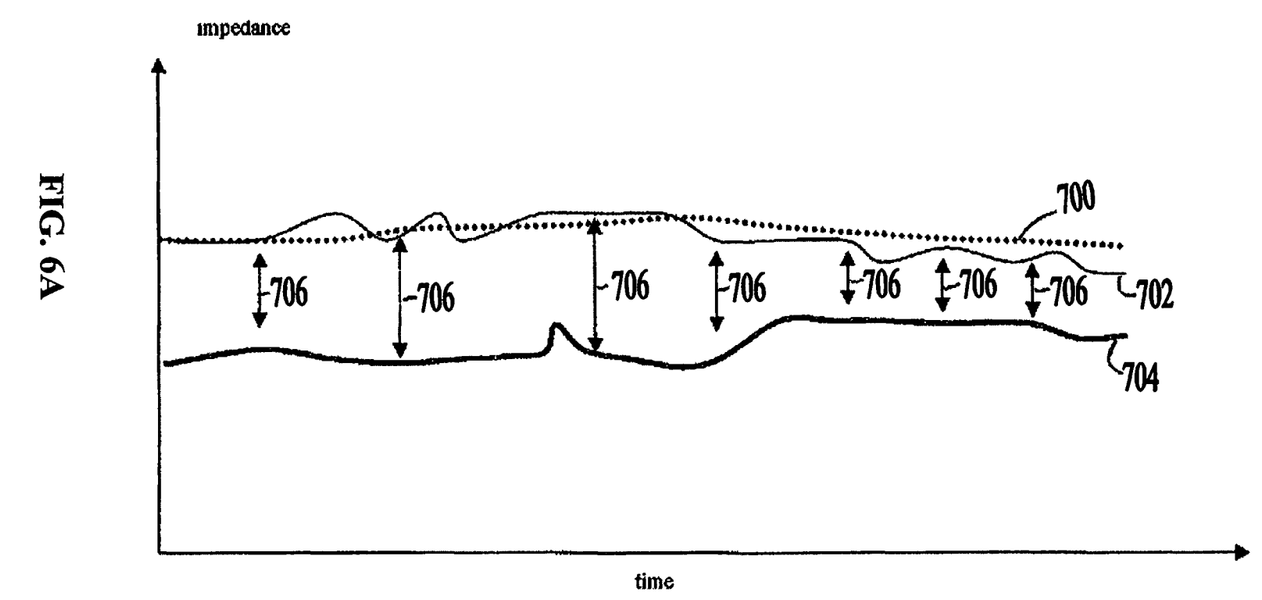
FIG. 6A is a graph showing the behavior between nighttime and daytime impedance measurements in an embodiment of the present invention.

FIG. 5 is an exemplary graphical representation of impedance data generated according to an embodiment of the present invention. Plot 406 in FIG. 5 illustrates a graphical representation of a calculated period average impedance 400 corresponding to the average of individual raw impedance measurements collected a predetermined number of times per day during a predetermined period of the day. A period average impedance value is then determined by calculating an average of the raw impedance measurements (e.g., one measurement every 20 minutes) generated during the predetermined time period, i.e., between 12 pm and 5 pm.

FIG. 5 also shows calculated values of a BL impedance 402, shown by a dashed line, and a STA impedance 404, shown by a solid line. These values 402, 404 are generated from the measured impedances, as described below. Plot 410 in FIG. 5 illustrates a graphical representation 408 of the difference between the calculated STA impedance and the calculated BL impedance as a percentage of the BL impedance. Plot 414 in FIG. 5 illustrates a graphical representation of the integral of the difference (IntDiff) 412 between the BL impedance 402 and the calculated period average impedance 400. The integral of the difference (IntDiff) 412 accumulates the difference between BL impedance 402 and the calculated period average impedances 400, and may be reset if the period average 400 exceeds the BL 402 (indicating dryness).

The goal of the design of the impedance sampling scheme in calculating the period average impedance is to exclude the contributions of undesirable impedance modifying factors, including all impedance changes that are unrelated to the patient's underlying fluid status, such as cardiac cycle, respiratory cycle, activity level, and posture. It is noteworthy that the undesirable impedance modifying factors operate on shorter time scales than true changes in the patient's fluid status, and therefore appropriate sampling and averaging schemes such as those examples presented above can be used to exclude the contributions of these undesirable impedance modifying factors.

Some of the techniques described above may be embodied as a computer-readable medium comprising instructions for a programmable processor such as microprocessor 224 or pacer timing/control circuitry 212 shown in FIG. 5. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above.

It is understood that the present invention could utilize any trending impedance algorithm that observes changes over time that are indicative of fluid overload, such as the algorithm discussed in U.S. Pat. Pub. 2004/0172080, filed on Dec. 3, 2003, titled Method and Apparatus for Detecting Change in Intrathoracic Electrical Impedance herein incorporated by reference in relevant part. However, other algorithms can be utilized in the present invention without departing from the spirit of the invention. The determination of fluid overload is made on a daily average focused on upright posture measurements. Certain embodiments of the invention include monitoring nocturnal (supine) and daily measurements and focusing on the variability between the two as an early indicator of general body fluid congestion (such as stomach edema) Such embodiments do not rely on just chest-based measurements. Existing edema monitoring techniques focus on pulmonary congestion and not the lower parts of the torso.

A significant fraction of patients with implanted devices have congestive heart failure and suffer from fluid overload requiring hospitalization. Automated detection of decreases in intrathoracic impedance may lead to advanced warning of fluid overload in patients with congestive heart failure.

Certain embodiments of the present invention provide early warning of fluid accumulation or dehydration in the thorax, most often as a result of cardiac decompensation during heart failure, and provide guidance to physicians or nurses to titrate medications like diuretics and beta blockers in heart failure patients. Patients with heart failure live in a delicate balance. Accumulation of fluid can result in frequent and lengthy hospitalizations. Medications can be effective in reducing the accumulation of fluids; but, to date, there is no accurate, minimally invasive metric of fluid accumulation. An implanted system to obtain measurements of intrathoracic impedance, as a surrogate measurement of fluid accumulation, has been described previously. Certain embodiments of the present invention include an algorithm for processing these measurements to determine a diurnal delta, e.g., a parallel comparison or cross checking of the measurements taken during the night against the measurements taken during the daytime. The diurnal delta may then provide a leading indicator of edema that may be evident only when a patient is in the supine position, which results in superior predictive value for detecting heart failure decompensation.

Certain method embodiments of the present invention operate by monitoring for rapid changes in impedance that exceed an algorithmically defined threshold of change, such as changing faster than expected (impedance decrease) which is indicative of thoracic fluid overload. In at least one such method embodiment, a parallel evaluation of impedance measurements are taken during the night for comparison/cross-checking against measurements taken during the day. The difference between the two, herein referred to as the diurnal delta, provides a leading indicator of the other sources of edema that may be evident in an ICD measurement vector only when the patient is in a supine position.

Figure 7:
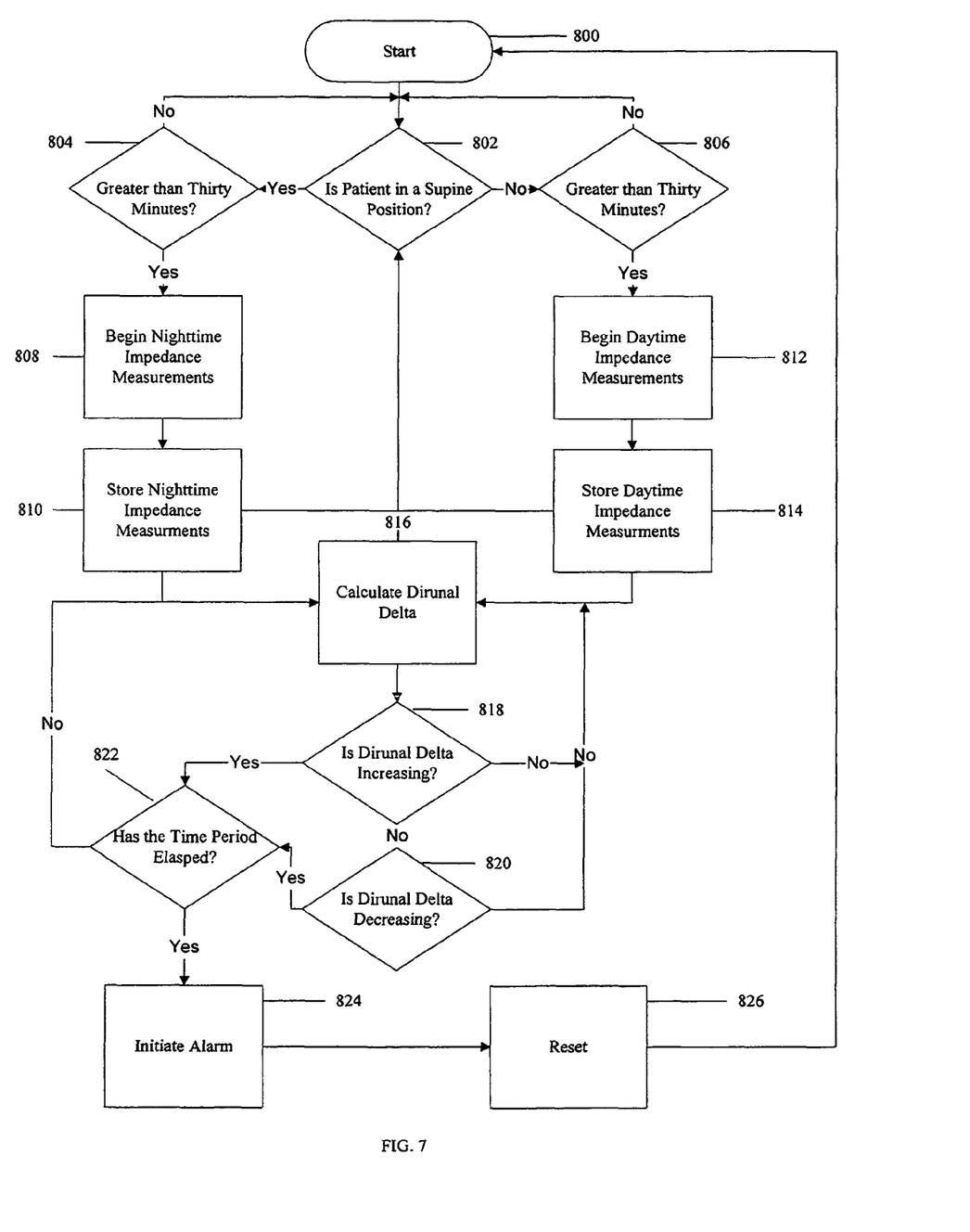
FIG. 7 is a flowchart diagram of an algorithm for measuring the difference between nighttime and daytime impedance measurements from a patient in an embodiment of the present invention.

With reference to FIG. 7, a graph showing the behavior between nighttime and daytime impedance measurements in an embodiment of the present invention is shown. This figure illustrates a long-term average measurement 700 (such as BL impedance described above), a daytime measurement 702 (such as the period average or the STA described above) and the nighttime measurement 704 (of the same type as daytime measurement 702) and a delta 706 or difference over time between daytime 702 and nighttime 704 measurements. It may be observed in this example that nighttime impedance 704 begins dropping in the presence of stable daytime measurement 702, which eventually declines as well. By observing delta 706 over time, a new predictive power can be added to impedance monitoring capabilities of present systems.

Although FIG. 7 displays the comparison between nighttime and daytime period averages or STA's, it is contemplated the nighttime and daytime comparisons be made between many types of impedance measurements. For instance, the delta 706 could be calculated from a night/day comparison of a long-term average impedance measurement or impedance measurement 408 in FIG. 5, representing the difference between the calculated STA impedance and the calculated BL impedance as a percentage of the BL impedance.

In another embodiment, the delta 706 may be calculated from a night/day comparison of IntDiff impedance calculations 412. In this embodiment, device 100 tracks night and day impedance measurements and accumulates the difference between each nighttime measured edema value and a rolling adapted average and the difference between each daytime measured edema value and a rolling adapted average. The difference between those two is accumulated over time and when that accumulation crosses a predetermined threshold (e.g., 70 ohms) over a predetermined period of time (e.g., three or four days), the program documents possible fluid overload. Device 100 can then generate an audible tone or communicate wirelessly through a network with a physician through a patient's home monitor. The physician can then receive the data in their office and determine whether possible accumulation is taking place.

In one embodiment, the physician sets a predetermined impedance threshold during implantation. For example, if the physician sets a limit of 60 ohms during implantation, the accumulated difference has to be more than 60 ohms over a predetermined period of time (also set by the physician). It is believed that typical impedance numbers range between 50-70 ohms. Therefore, if a patient was producing impedance measurements 10 ohms below the expected value and the 10 ohms measurements are consistent for the predetermined time frame, this will trigger a notification of possible fluid buildup. The program is adaptive and after a time limit, for example a month, the program initializes a new impedance base line depending on the impedance measurements over a month. Some patients will initialize at 50 ohms and some will initialize at 70 or 80 ohms. Then after the initialization, the program once again begins looking for deviation from the new base point.

The program is constantly looking for fluid increase over time, especially when patients are in a supine position. When patients lie down, fluid returns to the torso from their peripheral limbs and other areas. In prior systems, day-to-day measurements or measuring the impedance during the day was the most reliable because the measurements contained the least amount of noise as compared to nighttime measurements. For example, patient sleeping posture (right sided, left sided, on their back) could all influence nighttime measurements, and taken in isolation lead to noisy data. Thus nighttime measurements alone were not used very often. When patients are in a supine position, their particular posture when sleeping will generate unwanted noise. One embodiment does not ignore these nighttime measurements and instead utilizes them. As discussed above, one embodiment compares the daytime baseline against the nighttime baseline looking for a deviation between the two. By doing so, the program will detect a possible difference in impedance measurements possibly showing fluid that is returning to the torso when the patient is lying down. In prior systems, this fluid return would not be seen as measurements during the night were either not taken, not used, or too noisy. Moreover, when the measurements were taken the patient was upright walking around which often causes the fluid to return to the peripheries or dry up. Thus, this delta measurement between the daytime measurements and the nighttime measurements can be an early indicator of edema. The utilization of both aspects of the data—the more variable nighttime measurements and more stable daytime measurements is novel in combining the relative strengths of these signals.

It is generally accepted that the torso holds more fluid at night. However, one embodiment focuses on the delta measurement and not the fact that the measurement is going to be lower during the day. This embodiment focuses on whether the delta measurement is getting greater and greater over time. As is shown in FIG. 7, delta measurement 706 increases over time. Thus, this measurement can be used to detect onset of edema quicker than existing methods and systems, since the change in daily measurement 702 is not changing as quickly as the nighttime measurement 704. The physician and/or the device 100 may can provide therapy sooner.

One embodiment discloses a program that is looking for a change in the behavior between daytime measurement 702 and nighttime measurement 704. The program looks for a change in the delta between measurements 702 and 704. For example, if delta 706 has remained less than or equal to about 5 Ohms over a period of time and then suddenly delta 706 increases to 6, 7, and 8 ohms for a three or four day period, then the increase shows the possibility of fluid build up in the torso or other locations. In such an example, an alarm may be initiated to indicate the potential presence of edema. Thus one embodiment helps to prevent misinterpreting data where the measurements at night show a high impedance measurement and a low impedance measurement during the day that might otherwise lead to a conclusion of no edema. Instead the program of one embodiment, keeps track of the difference between the two and if this difference begins to grow, then the device provides an early warning or alarm that fluid is beginning to build up in the patient.

Impedance measurements during the day generally only show fluid buildup in the thoracic cavity caused by the pulmonary system. Therefore, if there is localized edema or edema in peripheral regions, such as the legs, these edemas may not be detected because they are not in the thoracic cavity. So one embodiment allows device 100 to see fluid seeping into the thoracic cavity as the patient sleeps or is in a supine position. Therefore, when device 100 begins to sense increased impedance measurements at night and relatively stable base line measurements during the day, device 100 may alert the physician that peripheral leg edema is sneaking into the lungs at night and then kind of fading out again during the day.

FIG. 7A shows a graph of exemplary nighttime and daytime impedance measurements in an embodiment of the present invention. Similar to FIG. 5, FIG. 7 shows exemplary daytime measurements 702, nighttime measurements 704 and the delta 706 therebetween. In contrast to FIG. 5, delta value 706 in FIG. 7A shows a decrease over time. A diminishing delta 706 may be a good indication of dehydration or hypovolemia. In this situation, daytime measurements 702 would begin closing in on nighttime measurements 704 showing that fluid is not flowing into the thoracic cavity and instead the thoracic cavity is increasingly drying out during the day. When alerted to this situation, the physician would be able to change patient therapy, such as altering diuretic administration and patient fluid intake instructions to restore appropriate fluid balance. As appropriate fluid levels were restored a more balanced and expected fluctuation between daytime and nighttime impedance would be restored and observed from the system. Dehydration can be very detrimental to the health of the patient as discussed in U.S. Pat. No. 6,922,592, filed on Apr. 4, 2001, titled Implantable medical device controlled by a non-invasive physiological data measurement device, herein incorporated by reference in relevant parts.

One embodiment discloses utilizing sensors 131 (FIG. 3) to indicate when the patient is in a supine position. One parameter that could be used would be the time of day in that most patients would be sleeping during the evening. Other sensor inputs could include an activity sensor, an accelerometer, or even a patient or physician override to begin the impedance measurements. Other sensor inputs could be used to determine whether the patient is in a supine position without departing from the spirit of the invention. It is further contemplated that nighttime measurements 704 would not be taken until the patient has been in a supine position for some period of time to let the fluid redistribute, and therefore device 100 is getting a real horizontal measurement.

With reference to FIG. 8, a flowchart diagram of an algorithm for measuring the difference between nighttime and daytime impedance measurements from a patient in an embodiment of the present invention is shown. As discussed above, the measurement of impedance usually does not begin until roughly 30 days after implantation of device 100. This is to help prevent any inaccurate readings and low impedance readings due to fluid buildup in the thoracic cavity as a result of the recovery from implantation of device 100. Therefore after a predetermined amount of time (e.g., 30 days) the program begins monitoring thoracic cavity impedance at state 800. Processor 224 then inquires as to whether the patient is in a supine position at state 802. As discussed above, this can be determined any number of ways, including using one or more sensors with or without use of the time of day. If it is determined that the patient is in a supine position, then processor 224 next inquires as to how long the patient has been in the supine position at state 804. As discussed above, it if helpful if the patient has been in the supine position for about a half hour so that body fluids can settle. If the patient is not in the supine position, then processor 224 moves to state 806 and inquires as to how long the patient has not been in the supine position for the same reasons stated above.

If at both state 804 and 806 processor 224 determines that the patient has been in neither state for the predetermined time, then processor 224 returns to state 802. At state 808 processor 224 begins collecting nighttime impedance measurements and stores the measurements in memory at state 810. At state 812 processor 224 begins collecting daytime impedance measurements and stores the measurements in memory at state 814. After state 810 and 814, processor returns to state 802 to confirm the patient is in the same position as the last measurement and the process continues as discussed above. At state 816, processor 225 collects and compares nighttime measurements 704 and daytime measurements 702 and calculates diurnal delta 706. At state 818, processor 224 determines if delta 706 has been increasing compared to prior measurements or has reached a predetermined high threshold value. At state 820, processor 224 determines if delta 706 has been decreasing compared to prior measurements or has reached a predetermined low threshold value. If delta 706 is neither increasing nor decreasing, then processor 224 returns to state 816 to calculate a new delta 706. If delta 706 is increasing or decreasing, then processor 224 proceeds to state 822 where processor 224 determines if the increasing or decreasing (or high value or low value) have been continuing and if the predetermined time limit has elapsed at state 822. As stated before, this time limit cold be three or four days, however, this limit could be any time frame and chosen by the implanting physician.

If the time limit has not elapsed, processor 224 returns to state 816. If the time limit has elapsed, processor 224 proceeds to state 824 where an alarm can be initiated, a therapy could be administered with an implantable device such as a drug pump administering diuretics, and/or a physician could be notified via a network hooked to a home monitor that communicates wirelessly with device 100. It is contemplated that the algorithm could also employ a weighted average, where the most recent data points are given more weight, in determining whether to initiate an alarm or not. Processor then proceeds to state 826 where the program is reset and returns to state 800 to begin the process again. The reset can be a full reset where all prior values are deleted and the process starts over or the reset can be a soft reset where only a couple of days of data are deleted.

In certain embodiments, the full reset or the soft reset may be manually initiated. That is, a physician or clinician may choose to reset all or a portion of the data. A reset may be performed via telemetry or via a pushbutton on the can.

Thus, embodiments of the ADVANCED THORACIC FLUID MONITORING CAPABILITY WITH IMPEDANCE are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. An implantable medical device for detection of changes in impedance in a patient, comprising:
    means for measuring impedances corresponding to a supine patient position and for measuring impedances corresponding to an upright patient position;
    means for generating a diurnal delta corresponding to the impedance differences between the supine and upright patient positions.

2. An implantable medical device according to claim 1, wherein the upright patient position is a period of time when the patient is likely in an upright position, and the supine patient position is a period of time when the patient is likely in a supine position.

3. An implantable medical device according to claim 1, wherein the upright and supine patient positions are the detected position of the patient based on sensor inputs.

4. An implantable medical device according to claim 1, wherein an alarm is initiated if the delta increases as compared to deltas generated in the past.

5. An implantable medical device according to claim 1, wherein an alarm is initiated if the delta decreases over a predetermined amount of time.

6. An implantable medical device according to claim 1, wherein the delta is the difference between the nighttime and daytime period average impedances.

7. An implantable medical device according to claim 1, wherein the delta is the difference between the nighttime and daytime integral differences, the integral differences being the integral of the difference between baseline impedances and period average impedances.

* * * * *